United States Patent
Lee et al.

(10) Patent No.: US 12,275,880 B2
(45) Date of Patent: Apr. 15, 2025

(54) GOLD NANOPARTICLE-FLUORESCENT HYBRID MATERIAL AND METHOD FOR PREPARING THE SAME

(71) Applicant: KYUNGPOOK NATIONAL UNIVERSITY INDUSTRY-ACADEMIC COOPERATION FOUNDATION, Daegu (KR)

(72) Inventors: Hye Jin Lee, Daegu (KR); Eun Seo Goh, Seoul (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 708 days.

(21) Appl. No.: 17/627,429

(22) PCT Filed: Oct. 18, 2019

(86) PCT No.: PCT/KR2019/013699
§ 371 (c)(1),
(2) Date: Jan. 14, 2022

(87) PCT Pub. No.: WO2021/010545
PCT Pub. Date: Jan. 21, 2021

(65) Prior Publication Data
US 2022/0259494 A1   Aug. 18, 2022

(30) Foreign Application Priority Data
Jul. 17, 2019   (KR) .................. 10-2019-0086557

(51) Int. Cl.
*C09K 11/65*   (2006.01)
*C09K 11/02*   (2006.01)
(Continued)

(52) U.S. Cl.
CPC ............ *C09K 11/65* (2013.01); *C09K 11/025* (2013.01); *C09K 11/58* (2013.01); *G01N 21/6428* (2013.01); *G01N 33/588* (2013.01)

(58) Field of Classification Search
CPC ....... C09K 11/65; C09K 11/58; C09K 11/025; G01N 21/6428; G01N 53/588
See application file for complete search history.

(56) References Cited

FOREIGN PATENT DOCUMENTS

| CN | 106983874 A | 7/2017 |
| JP | 2004-300253 A | 10/2004 |

(Continued)

OTHER PUBLICATIONS

Niu et al, "Gold Rod-Polyethylene Glycol-Carbon Dot Nanohybrids as Phototheranostic Probes", Nanomaterials, 2018, vol. 8, Issue 9, 706, pp. 1-12, Sep. 10, 2018.*

(Continued)

*Primary Examiner* — C Melissa Koslow
(74) *Attorney, Agent, or Firm* — NSIP Law

(57) ABSTRACT

The present invention relates to a gold nanoparticle-fluorescent hybrid material with improved fluorescence intensity and stability and a method for preparing the same. More specifically, the present invention relates to a gold nanoparticle-fluorescent hybrid material including gold nanoparticles, each of which is a polyhedron surrounded by 6 quadrilaterals, carbon quantum dots, and a polyglycol linking the gold nanoparticles with the carbon quantum dots, a method for preparing the hybrid material, a biosensor using the hybrid material, and a light emitting device for a display using the hybrid material.

17 Claims, 12 Drawing Sheets

(51) Int. Cl.
C09K 11/58 (2006.01)
G01N 21/64 (2006.01)
G01N 33/58 (2006.01)

(56) References Cited

FOREIGN PATENT DOCUMENTS

| KR | 10-2014-0059368 A | 5/2014 |
| KR | 10-2016-0120413 A | 10/2016 |
| KR | 10-1839700 B1 | 3/2018 |
| KR | 10-2019-0016354 A | 2/2019 |

OTHER PUBLICATIONS

Niu, Yuefang, et al. "Gold rod-polyethylene glycol-carbon dot nanohybrids as phototheranostic probes." Nanomaterials vol. 8 Issue 9; Sep. 10, 2018: pp. 1-12.
Korean Office Action issued on Jan. 11, 2024 in corresponding Korean Patent Application No. 201980098544.7.

* cited by examiner

[Fig. 1]
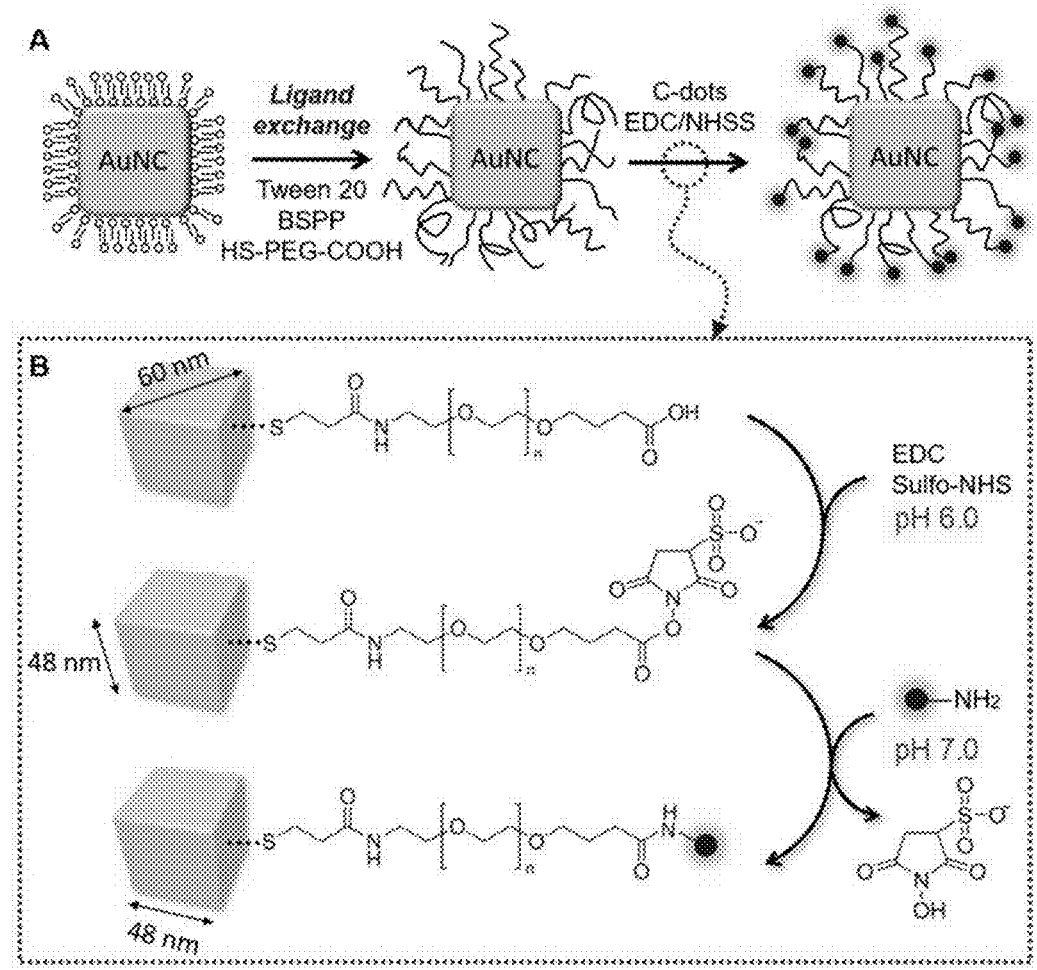

[Fig. 2A]
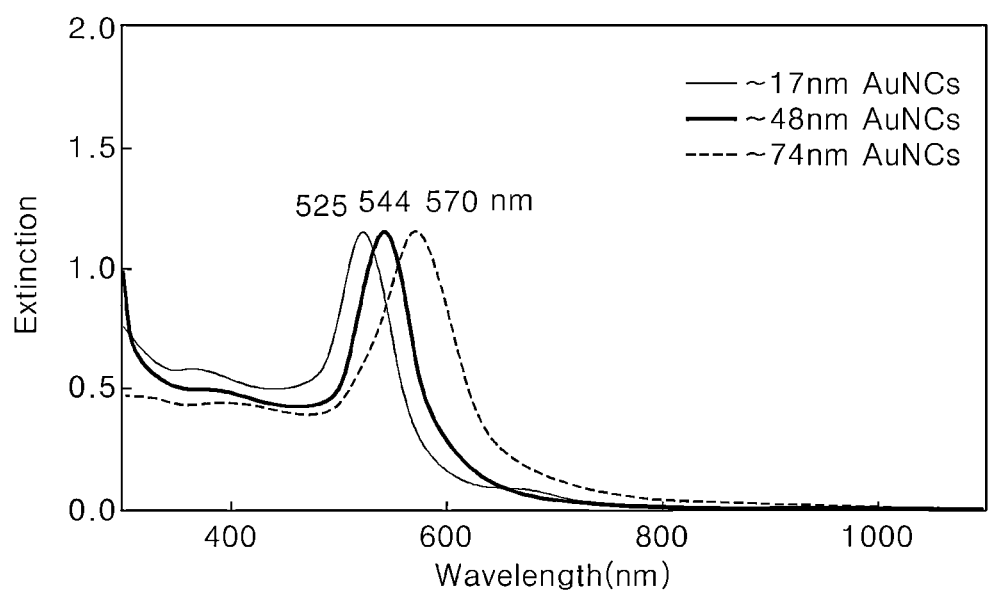

[Fig. 2B]
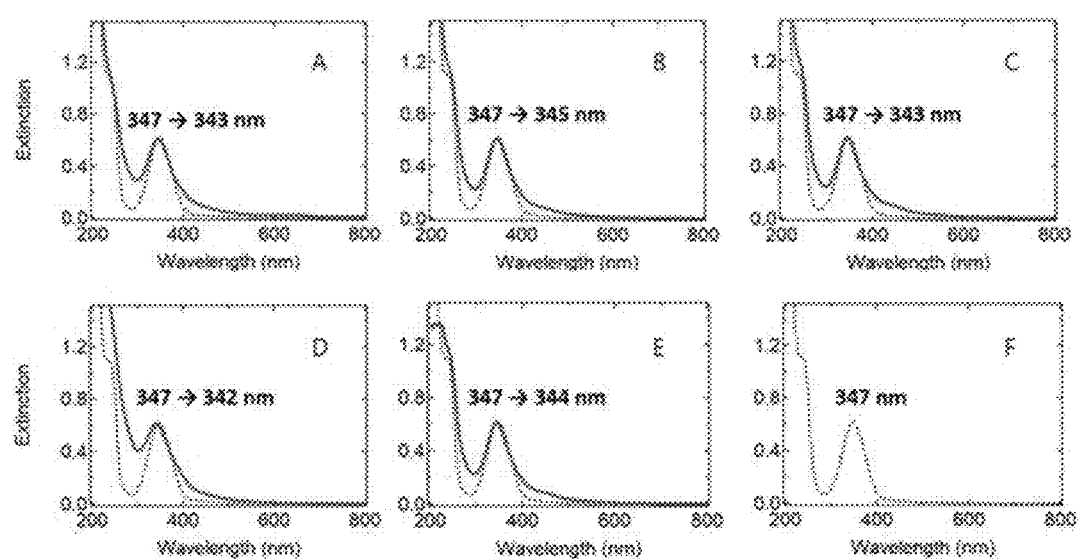

[Fig. 3A]
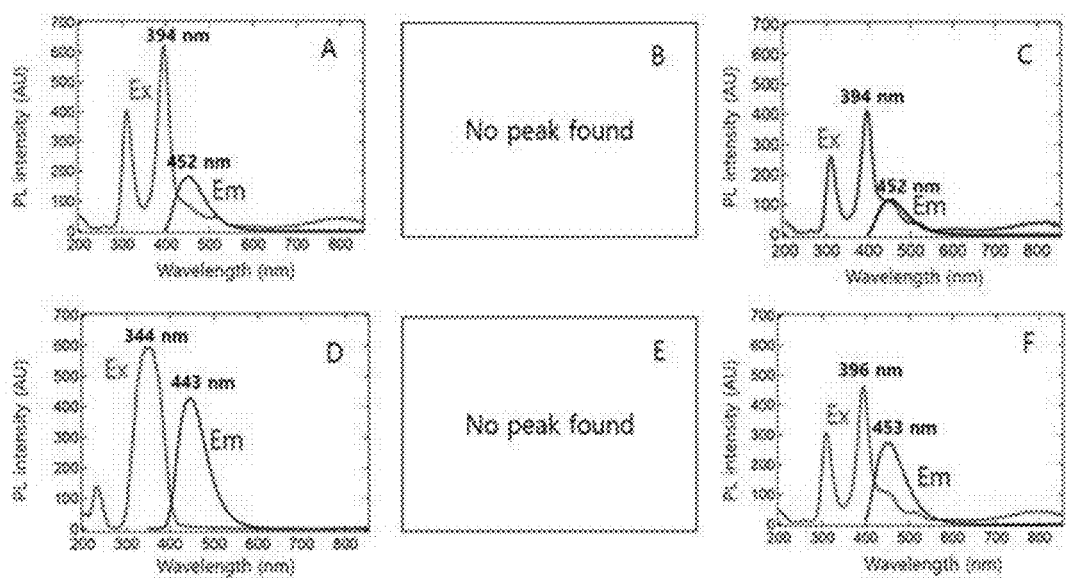

[Fig. 3B]
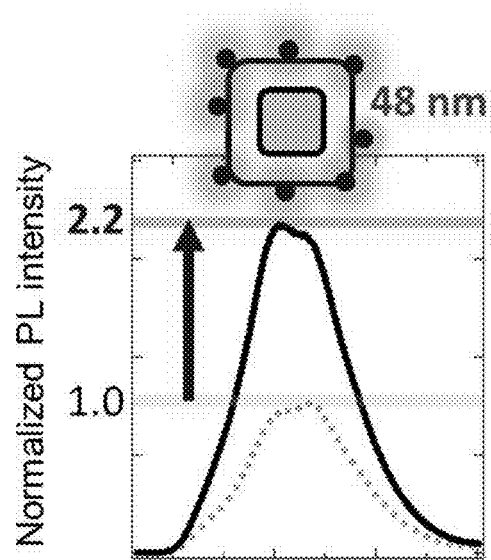
[Fig. 3C]
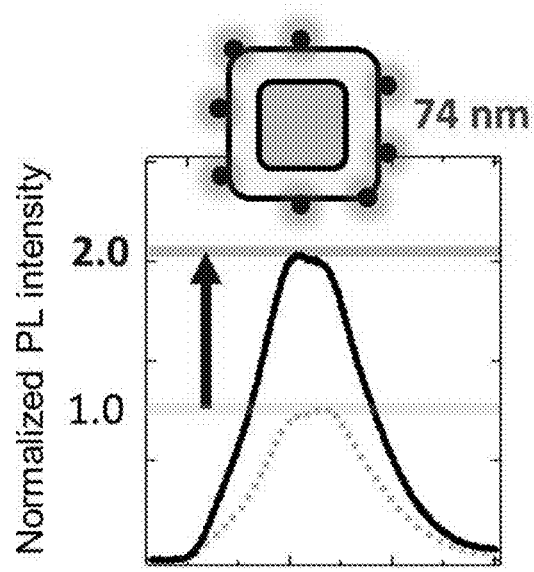

[Fig. 3D]
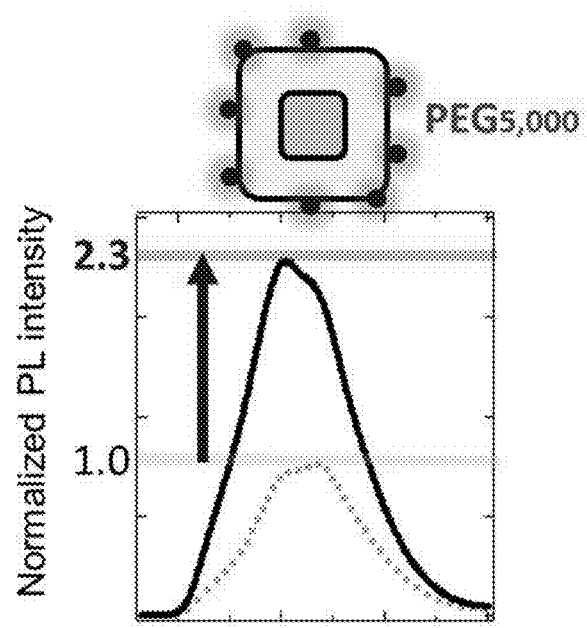
[Fig. 3E]
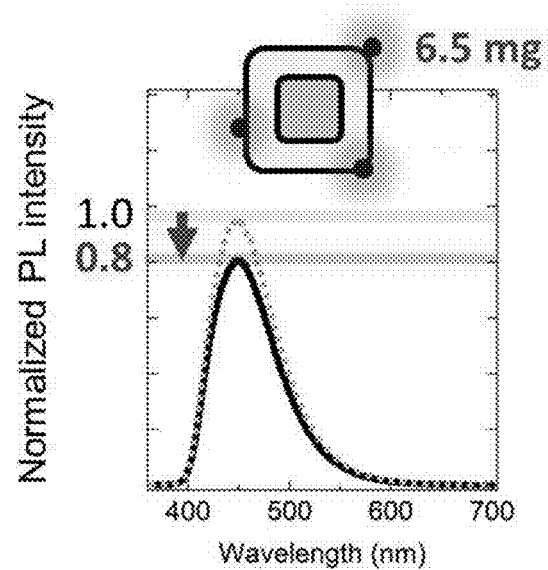

[Fig. 3F]
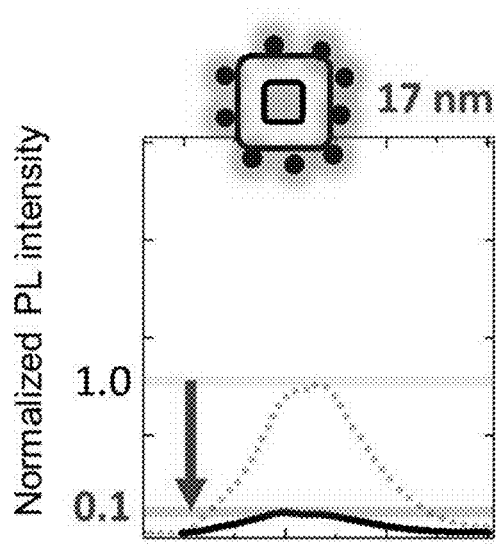
[Fig. 4A]
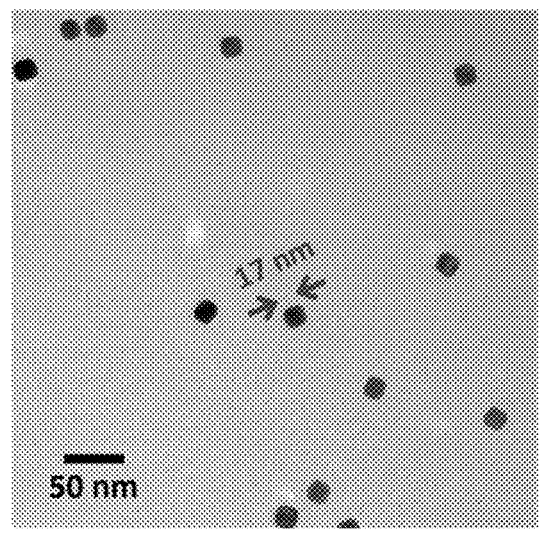

[Fig. 4B]
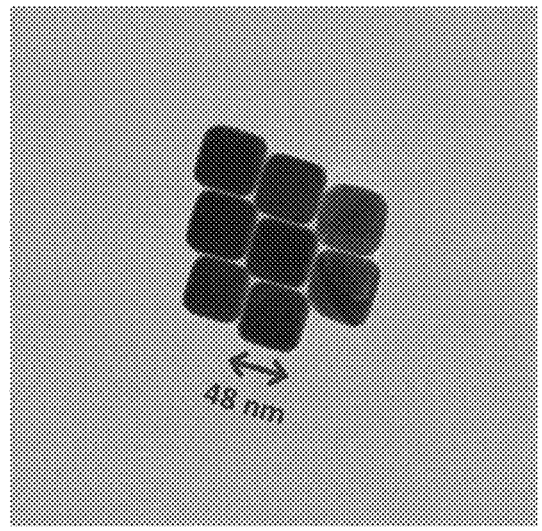
[Fig. 4C]
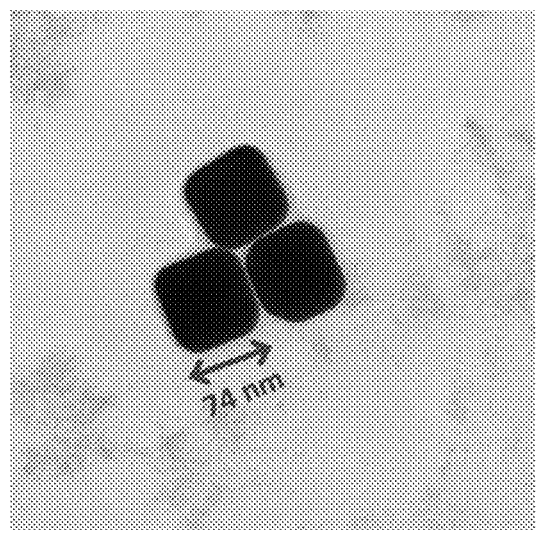

[Fig. 4D]
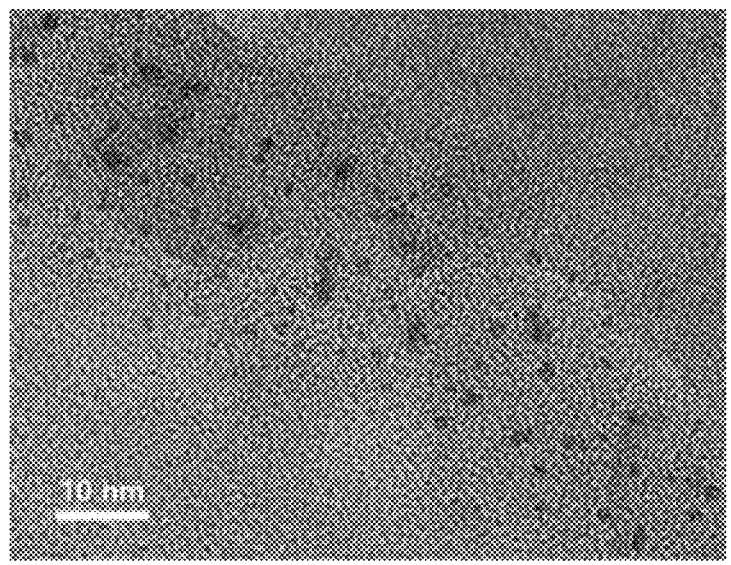
[Fig. 4E]
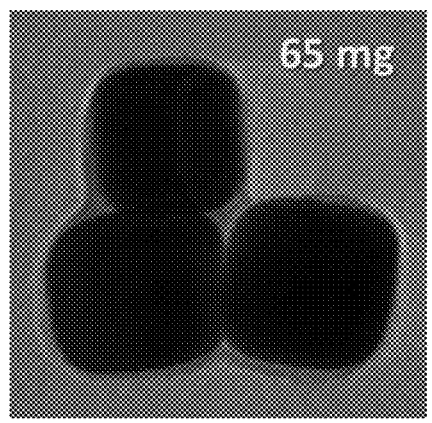

[Fig. 4F]
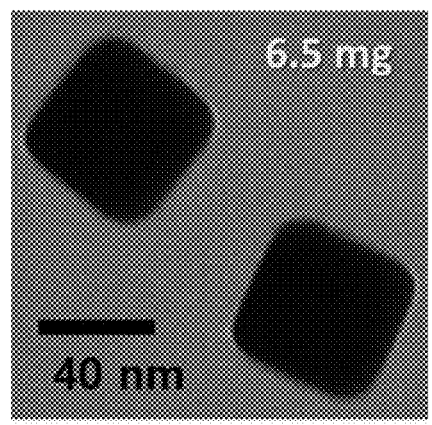
[Fig. 5A]
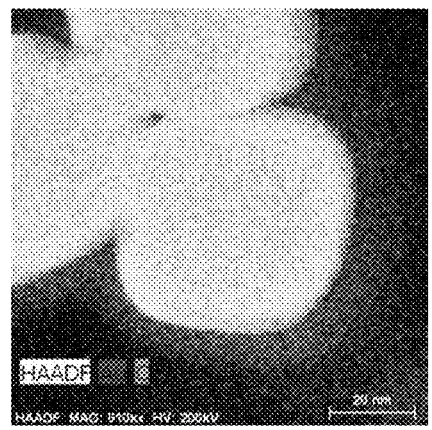

[Fig. 5B]
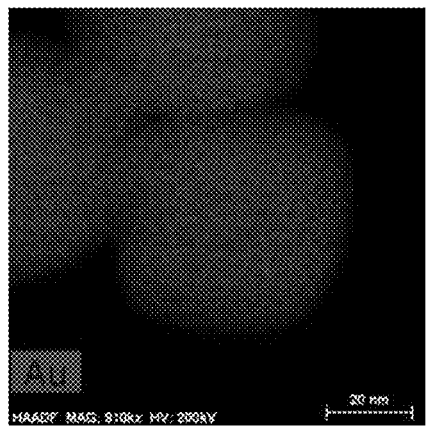
[Fig. 5C]
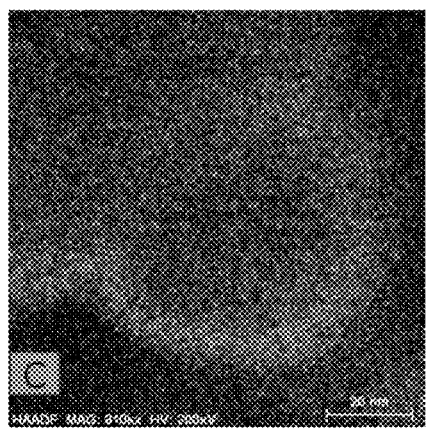
[Fig. 5D]
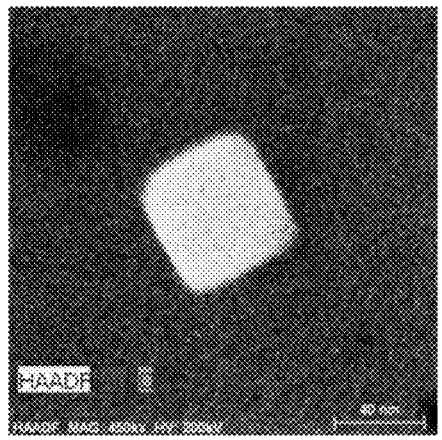

[Fig. 5E]
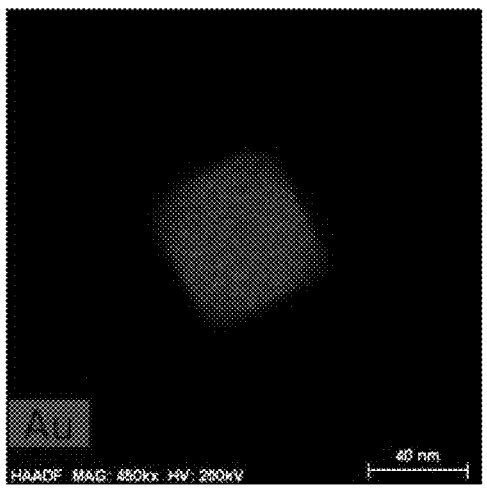
[Fig. 5F]
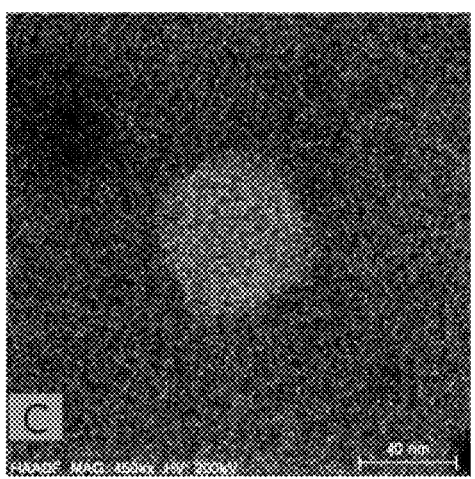

GOLD NANOPARTICLE-FLUORESCENT HYBRID MATERIAL AND METHOD FOR PREPARING THE SAME

CROSS REFERENCE TO RELATED APPLICATIONS

This application is a U.S. National Stage Application of International Application No. PCT/KR2019/013669, filed on Oct. 18, 2019, which claims the benefit under 35 USC 119(a) and 365(b) of Korean Patent Application No. 10-2019-0086557, filed on Jul. 17, 2019, in the Korean Intellectual Property Office, the entire disclosure of which is incorporated herein by reference for all purposes.

TECHNICAL FIELD

The present invention relates to a gold nanoparticle-fluorescent hybrid material with improved fluorescence intensity and stability and a method for preparing the same. More specifically, the present invention relates to a gold nanoparticle-fluorescent hybrid material including gold nanoparticles, each of which is a polyhedron surrounded by 6 quadrangular faces, carbon quantum dots, and a polyglycol linking the gold nanoparticles with the carbon quantum dots, a method for preparing the hybrid material, a biosensor using the hybrid material, and a light emitting device for a display using the hybrid material.

BACKGROUND ART

Fluorescent material is a generic term for a group of materials that emit fluorescence. This material emits fluorescence at any phase when irradiated with light. Fluorescent materials have been used in daily necessities such as cathode-ray tubes and fluorescent dyes and X-ray and electron microscopes. Recently, fluorescent materials have also been utilized in the field of light energy where light energy is absorbed by electrons in materials and photoelectrons are emitted from the materials, achieving light emission. A great deal of research has been conducted on fluorescent materials whose optical properties can be controlled. Thus, the application of fluorescent materials has been extended to the biological and medical fields using fluorescently labeled materials.

Quantum dots as fluorescent materials are self-illuminating nanoscale semiconductor crystals and are widely used in displays such as LCDs, LEDs, and OLEDs due to their ability to represent colors delicately and elaborately. However, quantum dots cause environmental pollution problems during synthesis and cannot be used in biological samples due to their toxicity. The synthesis of quantum dots requires complicated processes.

Carbon quantum dots (or carbon dots) with excellent characteristics in terms of luminescence, photostability, and electron transportability have recently attracted attention as replacements for quantum dot (QD) nanoparticles. Unlike quantum dots based on inorganic materials, carbon quantum dots (or carbon dot (C-dots)) are organic carbon nanomaterials containing carbon as a major element, hydrogen and oxygen as secondary elements, and optionally other elements such as nitrogen depending on raw materials. Carbon quantum dots exhibit fluorescent and semiconducting properties similar to those of inorganic quantum dots. In this regard, carbon quantum dots can find application in various fields, including bioimaging, sensors, light emitting diodes, lighting, organic solar cells, and photocatalysts.

However, carbon quantum dots are difficult to control, manipulate, and handle due to their amorphous shape and very low density. When carbon quantum dots are conjugated with other materials to have specific sizes and shapes, the brightness and fluorescence yield of the carbon quantum dots may decrease, and as a result, the optical properties of the carbon quantum dots may be unstable, thus limiting their use as fluorescent materials where uniform optical properties are needed.

DETAILED DESCRIPTION OF THE INVENTION

Problems to be Solved by the Invention

The present invention has been made in an effort to solve the above-described problems and one object of the present invention is to provide a gold nanoparticle-fluorescent hybrid material with a specific size and shape and improved optical properties.

A further object of the present invention is to provide a method for preparing a gold nanoparticle-fluorescent hybrid material.

Another object of the present invention is to provide a biosensor using the gold nanoparticle-fluorescent hybrid material.

Still another object of the present invention is to provide a light emitting device for a display using the gold nanoparticle-fluorescent hybrid material.

Means for Solving the Problems

One aspect of the present invention provides a gold nanoparticle-fluorescent hybrid material including gold nanoparticles, each of which is a polyhedron surrounded by 6 quadrangular faces, carbon quantum dots, and a polyglycol linking the gold nanoparticles with the carbon quantum dots.

A further aspect of the present invention provides a method for preparing a gold nanoparticle-fluorescent hybrid material, including synthesizing gold nanoparticles, each of which is a polyhedron surrounded by 6 quadrangular faces (first step), reacting the gold nanoparticles with a polyglycol having thiol and carboxyl groups (second step), and adding carbon quantum dots to the reaction product such that the carbon quantum dots are linked to the gold nanoparticles (third step).

Another aspect of the present invention provides a biosensor using the gold nanoparticle-fluorescent hybrid material.

Another aspect of the present invention provides a light emitting device for a display using the gold nanoparticle-fluorescent hybrid material.

Effects of the Invention

The gold nanoparticle-fluorescent hybrid material of the present invention exhibits a metal-enhanced fluorescence (MEF) effect between the gold nanoparticles and the carbon quantum dots and a fluorescent enhancement depending on the distance between the gold nanoparticles and the carbon quantum dots or the concentration of the carbon quantum dots. Due to these effects, the fluorescence intensity of the hybrid material can be effectively controlled.

In addition, the hybrid material of the present invention has a long lifetime, is simple to synthesize, and shows less toxicity compared to conventional fluorescent materials. Furthermore, the hybrid material of the present invention can be stored for a long period of time to achieve improved economic efficiency because the gold nanoparticles are very chemically stable. Moreover, the optical properties of the hybrid material according to the present invention are easy to control, regulate, and handle.

BRIEF DESCRIPTION OF THE DRAWINGS

FIG. 1 shows a process for synthesizing gold nanoparticle-fluorescent hybrid materials in Examples 2-4 and Comparative Examples 1-2.

FIG. 2a shows absorption spectra of gold nanoparticles (17 nm, 48 nm, 74 nm) synthesized in Examples 2-4 and Comparative Examples 1-2.

FIG. 2b compares peak absorption spectra of gold nanoparticle-fluorescent hybrid materials A-E of Examples 2-4 and Comparative Examples 1-2 and carbon quantum dots F of Comparative Example 3.

FIG. 3a shows absorption and emission spectra of gold nanoparticle-fluorescent hybrid materials A-E of Examples 2-4 and Comparative Examples 1-2 and carbon quantum dots F of Comparative Example 3.

FIG. 3b shows the emission intensity of a gold nanoparticle-fluorescent hybrid material A of Example 2.

FIG. 3c shows the emission intensity of a gold nanoparticle-fluorescent hybrid material B of Example 3.

FIG. 3d shows the emission intensity of a gold nanoparticle-fluorescent hybrid material C of Example 4.

FIG. 3e shows the emission intensity of a gold nanoparticle-fluorescent hybrid material D of Comparative Example 1.

FIG. 3f shows the emission intensity of a gold nanoparticle-fluorescent hybrid material E of Comparative Example 2.

FIG. 4a is a TEM image of gold nanoparticles (17 nm) synthesized in Comparative Example 2.

FIG. 4b is a TEM image of gold nanoparticles (48 nm) synthesized in Example 2.

FIG. 4c is a TEM image of gold nanoparticles (74 nm) synthesized in Example 3.

FIG. 4d is a HR-TEM image of carbon quantum dots F of Comparative Example 3.

FIG. 4e is a TEM image of a gold nanoparticle-fluorescent hybrid material A prepared in Example 2.

FIG. 4f is a TEM image of a gold nanoparticle-fluorescent hybrid material D prepared in Comparative Example 1.

FIG. 5a is an EDS mapping image showing the distributions of gold (Au, red) and carbon (C, green) as elements of a gold nanoparticle-fluorescent hybrid material A synthesized in Example 2.

FIG. 5b is an EDS mapping image showing the distribution of gold (Au, red) as an element of a gold nanoparticle-fluorescent hybrid material A synthesized in Example 2.

FIG. 5c is an EDS mapping image showing the distribution of carbon (C, green) as an element of a gold nanoparticle-fluorescent hybrid material A synthesized in Example 2.

FIG. 5d is an EDS mapping image showing the distributions of gold (Au, red) and carbon (C, green) as elements of a gold nanoparticle-polyglycol structure synthesized in Example 2.

FIG. 5e is an EDS mapping image showing the distribution of gold (Au, red) as an element of a gold nanoparticle-polyglycol structure synthesized in Example 2.

FIG. 5f is an EDS mapping image showing the distribution of carbon (C, green) as an element of a gold nanoparticle-polyglycol structure synthesized in Example 2.

MODE FOR CARRYING OUT THE INVENTION

Throughout this specification, unless the context requires otherwise, the words "comprise (include)," "comprises (includes)," and "comprising (including)" will be understood to imply the inclusion of other components but not the exclusion of other components. The terminology used herein is for the purpose of describing embodiments only and is not intended to limit the present invention. As used herein, the singular forms "a", "an" and "the" are intended to include the plural forms as well, unless the context clearly indicates otherwise.

The present invention will now be described in more detail.

The present invention is directed to a gold nanoparticle-fluorescent hybrid material with improved fluorescence intensity and stability and a method for preparing the hybrid material.

In one aspect, the present invention provides a gold nanoparticle-fluorescent hybrid material including gold nanoparticles, each of which is a polyhedron surrounded by 6 quadrangular faces, carbon quantum dots, and a polyglycol linking the gold nanoparticles with the carbon quantum dots.

Each of the gold nanoparticles may be a polyhedron surrounded by one or more faces selected from the group consisting of rectangular, square, rhombic, trapezoidal, parallelogram, and kite-like faces. The polyhedron may be a three-dimensional hexahedron with 6 quadrangular faces in which three faces meet at one vertex. The three-dimensional hexahedron may be a kind of quadrangular prism with 12 edges and 8 vertices. Preferably, the polyhedron may be a three-dimensional cube with 6 square faces in which three faces meet at one vertex. The three-dimensional cube may be a square prism with 12 edges and 8 vertices. The square prism can also be referred to as a "cube".

The gold nanoparticles may be a hexahedron in the form of a quadrangular prism. In this case, each edge of the hexahedron has a length of 20 to 100 nm, preferably 40 to 80 nm. If the length of each edge of the gold nanoparticles is less than 20 nm or exceeds 100 nm, the fluorescence intensity of the gold nanoparticle-fluorescent hybrid material may be lower than that of the original fluorescents (quenching effect).

The polyglycol may be added to link the gold nanoparticles with the fluorescents. The polyglycol may be connected to the surface of the gold nanoparticles by a ligand exchange reaction and may form covalent bonds with the carbon quantum dots to form the gold nanoparticle-fluorescent hybrid material. That is, the polyglycol can serve as a linker through which the gold nanoparticles are bonded to the fluorescents or a spacer to maintain or adjust the distance between the gold nanoparticles and the fluorescents. Preferably, the polyglycol has thiol (SH) and carboxyl (COOH) groups at both ends. The gold nanoparticle-fluorescent hybrid material of the present invention is formed by a ligand exchange reaction between the thiol group of the polyglycol and the gold nanoparticles and covalent bonding (amide bonding) between the carboxyl group of the polyglycol and the carbon quantum dots.

The molecular weight of the polyglycol is not limited as long as its theoretical value is at least 100. The molecular weight of the polyglycol is preferably 200 to 20,000. The polyglycol may surround the gold nanoparticles and its length may depend on not only its molecular weight but also the distance D between the polyglycol molecules on the surface of the gold nanoparticles.

When the distance D is larger than the Flory radius $R_f$, the polyglycol may aggregate to have a ball-like shape. Meanwhile, when the distance D is smaller than the Flory radius $R_f$, the polyglycol may extend in a relatively straight line. Assuming that the polyglycol molecule has a circular shape, the Flory radius $R_f$ represents the radius occupied by the polyglycol molecule. In an aqueous solution, $R_f$ can be expressed as $R_f = 3.5 \text{ Å } \sqrt[3]{5} \times n^{3/5}$ where n is the number of repeating monomers per polyglycol molecule. In the Examples section that follows, a polyglycol having a molecular weight of 3000, 66 repeating units, and a theoretical length of 20 nm was used. In a real aqueous solution, however, the polyglycol surrounding the gold nanoparticles may be 10 nm to less than 20 nm.

The polyglycol is preferably selected from the group consisting of polyethylene glycol, polyoxyethylene, polyethylene oxide, α-mercapto-ω-carboxy-polyethylene glycol, mercapto polyethylene glycol acid, mercapto polyethylene glycol-carboxylic acid, mercapto polyoxyethylene-acetic acid, thiol-polyethylene glycol, thiol-polyethylene glycol-carboxylic acid, thiol-polyethylene glycol acid, polypropylene glycol, polyalkylene glycol, diethylene glycol, triethylene glycol, dipropylene glycol, hexylene glycol, butylene glycol, and mixtures thereof. The polyglycol is more preferably selected from the group consisting of polyethylene glycol, polyoxyethylene, polyethylene oxide, α-mercapto-ω-carboxy-polyethylene glycol, mercapto polyethylene glycol acid, mercapto polyethylene glycol-carboxylic acid, mercapto polyoxyethylene-acetic acid, thiol-polyethylene glycol, thiol-polyethylene glycol-carboxylic acid, thiol-polyethylene glycol acid, and mixtures thereof.

The carbon quantum dots may be prepared by a bottom-up method using citric acid and ethylenediamine as raw materials. The carbon quantum dots thus prepared exhibit a much higher fluorescence quantum yield (QY) and fluorescence intensity and are more soluble in water than carbon quantum dots containing only carbon atoms due to the presence of a very large number of amino groups (—$NH_3$).

The fluorescence brightness of the hybrid material according to the present invention may be controlled by varying the concentration of the carbon quantum dots, the distance between the gold nanoparticles and the carbon quantum dots or the size of the gold nanoparticles. Since the carbon quantum dots are linked with and coated on the surface of the gold nanoparticles, the hybrid material is in the form of particles that have a uniform size, morphology, shape, and density, making it easy to handle.

It is known that conventional carbon quantum dots may become optically unstable because they lost their brightness or fluorescence quantum yield (QY) when linked to other materials or particles. Particularly, it is known that quenching occurs due to energy transfer when gold nanoparticles are linked or bonded with fluorescents and causes a decrease in the fluorescence of the fluorescents.

In contrast, the hybrid material of the present invention can exhibit a metal-enhanced fluorescence (MEF) (surface enhanced fluorescence (SEF), plasmon enhanced fluorescence or metal-induced fluorescent enhancement (MIFE)) effect between the gold nanoparticles and the carbon quantum dots due to the presence of the cubic gold nanoparticles, the carbon quantum dots, and the polyglycol. The metal-enhanced fluorescence effect refers to a phenomenon in which when a specific metal is covalently or non-covalently bonded to a fluorescent spaced a distance therefrom, the resulting hybrid material has an increased luminous efficiency and emits light whose brightness is greater than the maximum value of the original fluorescent. The causes of this effect may vary but the most common cause is that the interaction between the metal and the fluorescent changes the energy path for light emission.

Silver with a narrow plasmon band and high scattering efficiency has been widely used for metal-enhanced fluorescence and Ag@$SiO_2$ (silver particle-silicon spacer) platforms are mainly used at present. The hybrid material of the present invention is beyond these platforms and can be considered a new type of single nanoparticle sensing platform. The gold nanoparticles used in the hybrid material of the present invention are chemically more stable than silver, are convenient to synthesize, can be stored for an extended period of time, are advantageous from an economic viewpoint, and have a wide range of applications.

Preferably, the distance between the gold nanoparticles and the carbon quantum dots in the hybrid material of the present invention may be 5 nm to 20 nm. If the distance is smaller than 5 nm, fluorescence may be reduced. Meanwhile, if the distance exceeds 20 nm, the fluorescence intensity of the hybrid material may be lower than its maximum value.

The hybrid material may include 0.01 to 10 mg of the carbon quantum dots per 1 optical density (OD) of the gold nanoparticles. Preferably, the hybrid material includes 0.01 to 1 mg of the carbon quantum dots per 1 optical density (OD) of the gold nanoparticles. If the bonding ratio between the gold nanoparticles and the carbon quantum dots is out of the range defined above, fluorescence may be quenched.

In a further aspect, the present invention provides a method for preparing a gold nanoparticle-fluorescent hybrid material, including synthesizing gold nanoparticles, each of which is a polyhedron surrounded by 6 quadrangular faces (first step), reacting the gold nanoparticles with a polyglycol (second step), and adding carbon quantum dots to the reaction product such that the carbon quantum dots are linked to the gold nanoparticles (third step).

Each of the gold nanoparticles used in the method of the present invention may be a three-dimensional hexahedron (cube) with 6 quadrangular faces in which three faces meet at one vertex. The three-dimensional hexahedron may be a square prism with 12 edges and 8 vertices. The square prism can be referred to as a "cube". Each of the gold nanoparticles may be a polyhedron surrounded by one or more faces selected from the group consisting of rectangular, square, rhombic, trapezoidal, parallelogram, and kite-like faces. Each of the edges (line segments) of these faces has a length of 20 to 100 nm, preferably 40 to 80 nm. If the length of each edge of the gold nanoparticles is less than 20 nm or exceeds 100 nm, the fluorescence intensity of a final gold nanoparticle-fluorescent hybrid material may be lower than that of the original fluorescents (quenching effect).

The polyglycol is preferably selected from the group consisting of polyethylene glycol, polyoxyethylene, polyethylene oxide, α-mercapto-ω-carboxy-polyethylene glycol, mercapto polyethylene glycol acid, mercapto polyethylene glycol-carboxylic acid, mercapto polyoxyethylene-acetic acid, thiol-polyethylene glycol, thiol-polyethylene glycol-carboxylic acid, thiol-polyethylene glycol acid, polypropylene glycol, polyalkylene glycol, diethylene glycol, triethylene glycol, dipropylene glycol, hexylene glycol, butylene glycol, and mixtures thereof. The polyglycol is more preferably selected from the group consisting of polyethylene glycol, polyoxyethylene, polyethylene oxide, α-mercapto-ω-carboxy-polyethylene glycol, mercapto polyethylene glycol acid, mercapto polyethylene glycol-carboxylic acid, mercapto polyoxyethylene-acetic acid, thiol-polyethylene glycol, thiol-polyethylene glycol-carboxylic acid, thiol-polyethylene glycol acid, and mixtures thereof. The polyglycol may be added to link the gold nanoparticles with the fluorescents. The polyglycol may be connected to the surface of the gold nanoparticles by a ligand exchange reaction and may form covalent bonds with the carbon quantum dots to form the gold nanoparticle-fluorescent hybrid material. That is, the polyglycol can serve as a linker through which the gold nanoparticles are bonded to the fluorescents or a spacer to maintain or adjust the distance between the gold nanoparticles and the fluorescents. Preferably, the polyglycol has thiol (SH) and carboxyl (COOH) groups at both ends. The gold nanoparticle-fluorescent hybrid material is formed by a ligand exchange reaction between the thiol group of the polyglycol and the gold nanoparticles and covalent bonding (amide bonding) between the carboxyl group of the polyglycol and the carbon quantum dots.

The molecular weight of the polyglycol is not limited as long as its theoretical value is at least 100. The molecular weight of the polyglycol is preferably 200 to 20,000. The polyglycol may surround the gold nanoparticles and its length may depend on not only its molecular weight but also the distance D between the polyglycol molecules on the surface of the gold nanoparticles.

In the third step of the method according to the present invention, at least one crosslinking agent may be added. The crosslinking agent may be selected from the group consisting of dicyclohexyl carbodiimide (DCC), 1-ethyl-3-(3-dimethylaminopropyl)carbodiimide hydrochloride (EDC), 1-cyclohexyl-3-(2-morpholinoethyl)carbodiimide (CMC), diisopropyl carbodiimide (DIC), N-hydroxysuccinimide (NHS), and N-hydroxysulfosuccinimide sodium salt (NHSS). Preferably, the crosslinking agent is selected from the group consisting of 1-ethyl-3-(3-dimethylaminopropyl) carbodiimide hydrochloride (EDC), N-hydroxysuccinimide (NHS), and N-hydroxysulfosuccinimide sodium salt (NHSS).

The addition of the polyglycol or the crosslinking agent allows the gold nanoparticles and the polyglycol to undergo a ligand exchange reaction and the carbon quantum dots and the polyglycol to form covalent bonds (amide bonds). As a result of the bonding and the reaction, the gold nanoparticles can be bonded to the carbon quantum dots and the distance between the gold nanoparticles and the carbon quantum dots can be maintained or adjusted.

The distance between the gold nanoparticles and the carbon quantum dots may be 5 nm to 20 nm. If the distance is smaller than 5 nm, fluorescence may be reduced. Meanwhile, if the distance exceeds 20 nm, the fluorescence intensity of the hybrid material may be lower than its maximum value.

The carbon quantum dots may be used in an amount of 0.01 to 10 mg per 1 optical density (OD) of the gold nanoparticles to form the hybrid material. Preferably, the carbon quantum dots are used in an amount of 0.01 to 1 mg per 1 optical density (OD) of the gold nanoparticles. If the bonding ratio between the gold nanoparticles and the carbon quantum dots is out of the range defined above, fluorescence may be quenched.

In another aspect, the present invention provides a biosensor using a gold nanoparticle-fluorescent hybrid material.

Details of the hybrid material used in the biosensor of the present invention are the same as or similar to those described above and a description thereof will be thus omitted.

In another aspect, the present invention provides a light emitting device for a display using a gold nanoparticle-fluorescent hybrid material.

Details of the hybrid material used in the light emitting device of the present invention are the same as or similar to those described above and a description thereof will be thus omitted.

The present invention will be more specifically described with reference to the following examples. However, these examples are provided for illustrative purposes only and are not intended to limit the scope of the present invention. In addition, these examples are provided so that the disclosure of the present invention will be thorough and complete, and will fully convey the scope of the invention to those skilled in the art to which the present invention pertains.

EXAMPLES

Example 1—Synthesis of Carbon Quantum Dots (C-Dots)

1.051 g of citric acid and 335 µl of 50 w/w % ethylenediamine were added to 10 ml of distilled water, put into a preheated Teflon-lined stainless steel autoclave, heated at 150° C. for 5 h and 20 min, and distilled under reduced pressure to synthesize carbon quantum dots in a solid state (powder).

Example 2-1—Synthesis of Gold Nanoparticles (AuNCs) (48 nm)

In this example, gold nanoparticles whose one edge is 48 nm long were synthesized. First, 250 µl of a 0.01 M gold(III) chloride hydrate ($HAuCl_4$) solution was added to 7.5 ml of a 0.1 M hexadecyltrimethylammonium bromide (CTAB) solution and 600 µl of a 0.01 M sodium borohydride ($NaBH_4$) solution was added thereto. The mixture was stirred for 2 min and aged in an oven at 30° C. for 1 h to prepare a seed solution.

Thereafter, 6.4 ml of a 0.1 M CTAB solution was placed in another vial, 32 ml of distilled water, 800 µl of a 0.01 M $HAuCl_4$ solution, and 3.8 ml of a 0.1 M L-ascorbic acid solution were added to the vial, and 20 µl of a 10-fold dilution of the seed solution was added to the vial. The mixture was aged in an oven at 30° C. for 12 h to prepare a colloidal solution containing gold nanoparticles (48 nm).

Example 2-2—Ligand Exchange of the Gold Nanoparticles (CTAB, CTAC→PEG)

40 ml of the gold nanoparticle solution (optical density (OD) 1.156) was centrifuged 3 times at 6,000 g for 20 min, washed, and concentrated to a final volume of 4 ml to remove the excess CTAB or hexadecyltrimethylammonium chloride (CTAC) from the colloidal gold nanoparticle solution. To the concentrate were sequentially added 400 µl of a 2 vol % Tween 20 solution, 400 µl of a 0.1 M bis(p-sulfonatophenyl)phenylphosphine dihydrate dipotassium salt (BSPP) solution, 504 µl of a 1.6 mM O-(3-carboxypropyl)-O'-[2-(3-mercaptopropionylamino)ethyl]-polyethylene glycol ($M_w$ 3,000, HS-PEG3,000-COOH) solution, and 1200 µl of distilled water. The mixture was stirred at 900 rpm for 24 h. The reaction mixture was washed twice with distilled water in a centrifuge (6,000 g) for 30 min and at least 6 times with a 0.05 M 2-morpholinoethanesulfonic acid (MES, $C_6H_{13}NO_4S$) buffer at pH 6.0 and dispersed in MES buffer such that a final volume of 8 ml was attained. As a result, a colloidal solution was obtained in which the polyglycol was connected to the gold nanoparticles.

Example 2-3—Preparation of Gold Nanoparticle-Fluorescent Hybrid Material A 2 ml of the colloidal solution in which the polyglycol was connected to the gold nanoparticles was added to 8 ml of a 0.05 M MES buffer at pH 6.0, and then 5 mg of ethyl-3-(3-dimethylaminopropyl)carbodiimide (EDC) and 11 mg of sulfo-N-hydroxysuccinimide (sulfo-NHS), each of which had been previously dissolved in 200 µl of MES buffer, were rapidly added sequentially thereto. The mixture was sonicated for 15 min. 14 µl of 2-mercaptoethanol was added and sonicated for 10 min to induce complexation with EDC remaining after the reaction with the gold nanoparticles. To the resulting mixture were added 65 mg of the C-dots having amino groups (Example 1) and 65 µl of 5 M sodium hydroxide (NaOH), followed by sonication for 2 h to prepare a gold nanoparticle-fluorescent hybrid material A in which the polyglycol-connected gold nanoparticles were linked with the C-dots.

Example 3-1—Synthesis of Gold Nanoparticles (AuNCs) (74 nm)

In this example, gold nanoparticles whose one edge is 74 nm long were synthesized. First, 0.32 g of CTAC was dissolved in 5 ml of distilled water and 5 ml of a 0.5 mM $HAuCl_4$ solution and 450 µl of a 0.02 M $NaBH_4$ solution were sequentially added thereto. The mixture was stirred for 2 min and aged in an oven at 30° C. for 1 h to prepare a seed solution.

Thereafter, a solution of 0.32 g of CTAC in 9.625 ml of distilled water was placed in two different vials. 250 µl of a 0.01 M $HAuCl_4$ solution, 10 µl of a 0.01 M NaBr solution, and 90 µl of a 0.04 M L-ascorbic acid solution were added to each vial with stirring at a constant speed of 300 rpm. 25 µl of the seed solution was placed in only one of the vials and the reaction was allowed to proceed for 5 sec. When the color of the reaction solution turned red, the solution was added to the other vial. The reaction was allowed to proceed for 10 sec. The reaction solution was left standing for 15 min to prepare a colloidal solution containing gold nanoparticles (74 nm).

Example 3-2—Preparation of Gold Nanoparticle-Fluorescent Hybrid Material B

A colloidal solution in which a polyglycol was connected to the gold nanoparticles was prepared in the same manner as in Example 2-2, except that 2400 µl of a 2 vol % Tween 20 solution, 2400 µl of a 0.1 M bis(p-sulfonatophenyl)phenylphosphine dihydrate dipotassium salt (BSPP) solution, 3024 µl of a 1.6 mM HS-PEG3,000-COOH solution, and 7200 µl of distilled water were added. Thereafter, 65 mg of the C-dots having amino groups (Example 1) and 65 µl of 5 M sodium hydroxide (NaOH) were added. Then, a gold nanoparticle-fluorescent hybrid material B was prepared in the same manner as in Example 2-3. In the hybrid material B, the polyglycol-connected gold nanoparticles were linked with the C-dots.

Example 4—Preparation of Gold Nanoparticle-Fluorescent Hybrid Material C

A gold nanoparticle-fluorescent hybrid material C was prepared in the same manner as in Examples 2-1 to 2-3, except that 504 µl of a 1.6 mM O-(3-carboxypropyl)-O'-[2-(3-mercaptopropionylamino)ethyl]-polyethylene glycol ($M_w$ 5,000, HS-PEG5,000-COOH) solution was added.

Comparative Example 1—Preparation of Gold Nanoparticle-Fluorescent Hybrid Material D A gold nanoparticle-fluorescent hybrid material C was prepared in the same manner as in Examples 2-1 to 2-3, except that 6.5 mg of the C-dots and 45 µl of 5 M NaOH were added.

Comparative Example 2-1—Synthesis of Gold Nanoparticles (AuNCs) (17 nm)

In this example, gold nanoparticles whose one edge is 17 nm long were synthesized. First, 250 µl of a 0.01 M $HAuCl_4$ solution was added to 9.75 ml of a 0.1 M CTAB and 600 µl of a 0.01 M $NaBH_4$ solution was added thereto. The mixture was stirred for 3 min and aged in an oven at 27° C. for 3 h to prepare a 1-2 nm seed solution.

2 ml of a 0.2 M CTAC solution was placed in another vial. 1.5 ml of a 0.1 M L-ascorbic acid solution, 50 µl of the 1-2 nm seed solution, and 2 ml of a 0.5 mM $HAuCl_4$ solution were sequentially added to the vial with stirring at a constant speed of 300 rpm. The reaction was allowed to proceed for 15 min. The reaction solution was washed once with distilled water in a centrifuge (20600 g) for 30 min and dispersed in 1 ml of a 20 mM CTAC solution (a 10 nm seed solution).

Thereafter, 6 ml of a 0.1 M CTAC solution was placed in another vial and 30 µl of a 120 mM sodium bromide (NaBr) solution, 300 µl of the 10 nm seed solution, 390 µl of a 10 mM L-ascorbic acid solution, and 6 ml of a 0.5 mM $HAuCl_4$ solution were sequentially added to the vial with stirring at a speed of 500 rpm. The reaction was allowed to proceed for 25 min to form a colloidal solution containing gold nanoparticles (17 nm).

Comparative Example 2-2—Preparation of Gold Nanoparticle-Fluorescent Hybrid Material E A colloidal solution in which a polyglycol was connected to the gold nanoparticles was prepared in the same manner as in Example 2-2, except that 2800 µl of a 2 vol % Tween 20 solution, 2800 µl of a 0.1 M bis(p-sulfonatophenyl)phenylphosphine dihydrate dipotassium salt (BSPP) solution, 3528 µl of a 1.6 mM HS-PEG3,000-COOH solution, and 8400 µl of distilled water were added. Thereafter, 65 mg of the C-dots having amino groups (Example 1) and 65 µl of 5 M sodium hydroxide (NaOH) were added. Then, a gold nanoparticle-fluorescent hybrid material E was prepared in the same manner as in Example 2-3. In the hybrid material E, the polyglycol-connected gold nanoparticles were linked with the C-dots.

Comparative Example 3—Carbon Quantum Dots F

The carbon quantum dots synthesized in Example 1 were compared with the hybrid materials A-E (Examples 2-4 and Comparative Examples 1 and 2) (each 65 mg) according to the following experimental examples.

The edge lengths of the gold nanoparticles in the hybrid materials A-E (Examples 2-4 and Comparative Examples 1 and 2) and the carbon quantum dots F (Comparative Example 3), the molecular weights of the PEGs used, and the amounts of the carbon quantum dots added are shown in Table 1.

TABLE 1

|  | A | B | C | D | E | F |
|---|---|---|---|---|---|---|
| Gold nanoparticles (nm) | 48 | 74 | 48 | 48 | 17 | — |
| PEG ($M_w$) | 3000 | 3000 | 5000 | 3000 | 3000 | — |
| C-dots (mg) | 65 | 65 | 65 | 6.5 | 65 | 65 |

FIG. 1 shows the process for preparing the hybrid materials of Examples 2-4 and Comparative Examples 1-2.

EXPERIMENTAL EXAMPLES

Experimental Example 1—UV Spectrophotometer Measurement

The gold nanoparticles synthesized in Examples 2-4 and Comparative Examples 1-2, the hybrid materials A-E of Examples 2-4 and Comparative Examples 1-2, and the carbon quantum dots of Comparative Example 3 were placed in different cells and their absorption spectra were measured in the wavelength range of 190 nm to 1100 nm.

Experimental Example 2—PL Emission Measurement

The hybrid materials A-E of Examples 2-4 and Comparative Examples 1-2 and the carbon quantum dots F of Comparative Example 3 were placed in different cells and their fluorescence emission values were measured in the wavelength range of 365 nm-700 nm with an excitation wavelength of 365 nm.

Experimental Example 3—TEM Measurement

The gold nanoparticles synthesized in Examples 2-4 and Comparative Example 1 and the hybrid materials A-D of Examples 2-4 and Comparative Example 1 were placed on different TEM grids and observed using a bio transmission electron microscope (Bio-TEM). The carbon quantum dots F of Comparative Example 3 were placed on a TEM grid and observed using a field emission transmission electron microscope (FE-TEM).

Experimental Example 4—EDS Measurement

The gold nanoparticles (48 nm) synthesized in Example 2 and Comparative Example 1 and the hybrid materials A and D of Example 2 and Comparative Example 1 were placed on different TEM grids and observed using an energy dispersive spectrometer (EDS).

<Evaluation and Results>
Results 1—UV Spectrophotometer Measurement

FIGS. 2a and 2b show the absorbance values of the gold nanoparticles (17 nm, 48 nm, 74 nm) synthesized in Examples 2-4 and Comparative Examples 1-2, the hybrid materials A-E of Examples 2-4 and Comparative Examples 1-2, and the carbon quantum dots of Comparative Example 3, which were measured in Experimental Example 1.

In FIG. 2a, the gold nanoparticles (17 nm, 48 nm, 74 nm) showed single peaks (maximum absorption) in the visible region. The peak shifted to a longer wavelength as the size of the gold nanoparticles increased.

In FIG. 2b, the absorption spectra of the hybrid materials A-E showed blue-shifts, unlike that of the carbon quantum dots F. Each of the hybrid materials exhibited shoulder peaks on both sides of the maximum absorption peak, unlike the carbon quantum dots.

Result 2—PL Emission Spectra

The absorption and emission spectra of A-F (Examples 2-4 and Comparative Examples 1-3) measured in Experimental Example 2 are shown in FIG. 3a.

The spectra revealed that the ratios of the maximum emission values Em to the maximum absorption values Ex in the spectra of the hybrid material A of Example 2 and the hybrid material C of Example 3 (gold nanoparticles: 48 nm size, carbon quantum dots: 65 mg) decreased compared to those in the spectra of the hybrid material D of Comparative Example 1 (gold nanoparticles: 48 nm size, carbon quantum dots: 6.5 mg) and the carbon quantum dots F (65 mg) of Comparative Example 3. These results demonstrate that the size of the gold nanoparticles and the concentration of the carbon quantum dots used to prepare the hybrid material are factors affecting the optical properties of the hybrid material. The different ratios of the maximum emission values Em to the maximum absorption values Ex in the spectra of the hybrid materials A and C using PEGs with different molecular weights indicate that the length of the linker (PEG) linking the gold nanoparticles with the carbon quantum dots is a factor affecting the optical properties of the hybrid material.

The fluorescence emission spectra of A-E of Examples 2-4 and Comparative Examples 1-2 measured in Experimental Example 2 are shown in FIGS. 3b to 3f, respectively. In each of FIGS. 3b to 3f, the dotted line shows the fluorescence emission spectrum of the carbon quantum dots F of Comparative Example 3 where the peak serves as a reference (1.0) for fluorescence intensity.

Referring first to FIGS. 3b, 3c, and 3f, the fluorescent enhancements of the hybrid materials were compared based on the size of the gold nanoparticles. As a result, the fluorescent enhancement of the hybrid material prepared using the 48 nm sized gold nanoparticles was found to be stronger than those of the hybrid material prepared using the polyglycol of the same molecular weight and the larger sized gold nanoparticles and the hybrid material prepared using the carbon quantum dots of the same weight and the smaller sized gold nanoparticles. The second strongest fluorescent enhancement was found in the hybrid material prepared using the 74 nm sized gold nanoparticles and the weakest fluorescent enhancement was found in the hybrid material prepared using the 17 nm sized gold nanoparticles. Particularly, the fluorescence intensity of the hybrid material prepared using the 17 nm sized gold nanoparticles was much lower than that of the reference F. The fluorescence intensity of the hybrid material prepared using the 48 nm sized gold nanoparticles was at least twice than that of the reference F, demonstrating that the size of the gold nanoparticles affects the fluorescence intensity and fluorescent enhancement of the carbon quantum dots.

Referring next to FIGS. 3b and 3d, the fluorescent enhancements of the hybrid materials were compared based on the molecular weight of the polyglycol (PEG). As a result, the fluorescence intensity and fluorescent enhancement of the hybrid material prepared using the PEG with the higher molecular weight were found to be higher than those of the hybrid material prepared using the polyglycol with the lower higher molecular weight despite the use of the gold nanoparticles of the same size and the carbon quantum dots of the same weight.

Referring finally to FIGS. 3b and 3e, the fluorescent enhancements of the hybrid materials were compared based on the amount of the carbon quantum dots. As a result, the fluorescence intensity and enhanced fluorescence effect of the hybrid material prepared using the larger amount (i.e. higher concentration) of the carbon quantum dots were found to be higher than those of the hybrid material prepared using the smaller amount of the carbon quantum dots despite the use of the PEG of the same molecular weight and the gold nanoparticles of the same size. The hybrid material A prepared using 65 mg of the carbon quantum dots, the hybrid material D prepared using 6.5 mg of the carbon quantum dots, and the carbon quantum dots F (65 mg, reference) were compared for fluorescence intensity and fluorescent enhancement. As a result, the fluorescence intensity of the hybrid material D was reduced by only ~0.2 compared to that of the carbon quantum dots F although the amount of the carbon quantum dots used in the hybrid material D was different by a factor of 10 from that of the carbon quantum dots F. In contrast, the fluorescent enhancement of the hybrid material A prepared using the same amount of the carbon quantum dots was at least twice than that of the reference F. These results concluded that the linkage of the gold nanoparticles with the carbon quantum dots in the inventive hybrid material is effective in increasing the fluorescence intensity of the carbon quantum dots.

Result 3—TEM Images

TEM images of the gold nanoparticles (17 nm) synthesized in Comparative Example 2, the gold nanoparticles (48 nm) synthesized in Example 2, the gold nanoparticles (74 nm) synthesized in Example 3, the hybrid materials A and D, and the carbon quantum dots F were taken and are shown in FIGS. 4a to 4f, respectively. The TEM images of FIGS. 4a to 4c revealed that the gold nanoparticles were hexahedra with quadrangular faces consisting of 17 nm, 48 nm, and 74 nm line segments, respectively. The TEM images of the hybrid materials prepared using the 48 nm gold nanoparticles revealed that the use of the larger amount of the carbon quantum dots allowed a larger amount of the carbon quantum dots to be linked to the gold nanoparticles, leading to the formation of thicker coating layers surrounding the gold nanoparticles.

Result 4—EDS Images

EDS images of the hybrid material A synthesized in Example 2 were taken and are shown in FIGS. 5a to 5c.

The images revealed that the gold nanoparticles were located at the center of the hybrid material and were surrounded by the carbon quantum dots and the fluorescent-metal distance was ~10 nm.

EDS images of the reaction products of the gold nanoparticles (48 nm) and the polyglycol (before preparation of the hybrid material A (i.e. before bonding with the carbon quantum dots)) in Examples 2-1 and 2-2 were taken and are shown in FIGS. 5d to 5f.

Mapping was conducted for carbon (C in FIGS. 5A, 5C, 5D, and 5F) in the structure in which only the polyglycol was connected to the gold nanoparticles. As a result, only noise induced by the background carbon present in the TEM grid and the gold nanoparticles was observed. These observations show a clear difference from the hybrid material in which the gold nanoparticles were linked with the carbon quantum dots. The above results clearly demonstrate that the gold nanoparticles are linked with the carbon quantum dots to form the hybrid material.

The invention claimed is:

1. A gold nanoparticle-fluorescent hybrid material comprising gold nanoparticles, each of which is a polyhedron surrounded by 6 quadrangular faces, carbon quantum dots, and a polyglycol linking the gold nanoparticles with the carbon quantum dots.

2. The gold nanoparticle-fluorescent hybrid material according to claim 1, wherein each of the gold nanoparticles is a polyhedron surrounded by one or more quadrangular faces selected from the group consisting of rectangular, square, rhombic, trapezoidal, parallelogram, and kite-like faces.

3. The gold nanoparticle-fluorescent hybrid material according to claim 1, wherein the polyglycol has a molecular weight of 200 to 20,000.

4. The gold nanoparticle-fluorescent hybrid material according to claim 1, wherein the fluorescence brightness of the hybrid material is controlled by varying the concentration of the carbon quantum dots or the distance between the gold nanoparticles and the carbon quantum dots.

5. A method for preparing a gold nanoparticle-fluorescent hybrid material, comprising synthesizing gold nanoparticles, each of which is a polyhedron surrounded by 6 quadrangular faces (first step), reacting the gold nanoparticles with a polyglycol having thiol and carboxyl groups (second step), and adding carbon quantum dots to the reaction product such that the carbon quantum dots are linked to the gold nanoparticles (third step).

6. The method according to claim 5, wherein each of the gold nanoparticles is a polyhedron surrounded by one or more quadrangular faces selected from the group consisting of rectangular, square, rhombic, trapezoidal, parallelogram, and kite-like faces.

7. The method according to claim 6, wherein each edge of the quadrangular faces has a length of 20 to 100 nm.

8. The method according to claim 5, wherein the polyglycol has a molecular weight of 200 to 20,000.

9. The method according to claim 5, wherein at least one crosslinking agent selected from the group consisting of dicyclohexyl carbodiimide (DCC), 1-ethyl-3-(3-dimethyl-aminopropyl) carbodiimide hydrochloride (EDC), 1-cyclohexyl-3-(2-morpholinoethyl) carbodiimide (CMC), diisopropyl carbodiimide (DIC), N-hydroxysuccinimide (NHS), and N-hydroxysulfosuccinimide sodium salt (NHSS) is added in the third step.

10. A biosensor using the gold nanoparticle-fluorescent hybrid material according to claim 1.

11. A biosensor using the gold nanoparticle-fluorescent hybrid material according to claim 2.

12. A biosensor using the gold nanoparticle-fluorescent hybrid material according to claim 3.

13. A biosensor using the gold nanoparticle-fluorescent hybrid material according to claim 4.

14. A light emitting device for a display using the gold nanoparticle-fluorescent hybrid material according to claim 1.

15. A light emitting device for a display using the gold nanoparticle-fluorescent hybrid material according to claim 2.

16. A light emitting device for a display using the gold nanoparticle-fluorescent hybrid material according to claim 3.

17. A light emitting device for a display using the gold nanoparticle-fluorescent hybrid material according to claim 4.

* * * * *